United States Patent [19]
Hamilton et al.

[11] Patent Number: 5,846,979
[45] Date of Patent: Dec. 8, 1998

[54] N-OXIDES OF HETEROCYCLIC ESTERS, AMIDES, THIOESTERS, AND KETONES

[75] Inventors: Gregory S. Hamilton, Catonsville; Joseph P. Steiner, Hampstead; Eric S. Burak, Forest Hill, all of Md.

[73] Assignee: GPI NIL Holdings, Inc., Wilmington, Del.

[21] Appl. No.: 807,406

[22] Filed: Feb. 28, 1997

[51] Int. Cl.⁶ .................. A61K 31/47; A61K 31/445; C07D 211/02

[52] U.S. Cl. .................. 514/311; 514/314; 514/316; 514/318; 514/323; 514/320; 514/317; 514/326; 514/332; 514/331; 514/337; 514/336; 514/354; 514/423; 546/186; 546/193; 546/205; 546/168; 540/597; 540/602; 540/603; 540/607; 540/608; 518/527; 518/517; 518/518

[58] Field of Search .................. 540/597, 602, 540/603, 607, 608; 546/186, 193, 205, 168; 548/527, 517, 518; 514/316, 318, 323, 320, 317, 326, 332, 339, 337, 336, 354, 423, 314, 311

[56] References Cited

U.S. PATENT DOCUMENTS

| | | | |
|---|---|---|---|
| 5,192,773 | 3/1993 | Armistead et al. | 514/315 |
| 5,330,993 | 7/1994 | Armistead | 514/330 |
| 5,385,918 | 1/1995 | Connell et al. | 514/330 |
| 5,516,797 | 5/1996 | Armistead et al. | 514/548 |
| 5,543,423 | 8/1996 | Zelle et al. | 514/332 |

FOREIGN PATENT DOCUMENTS

| | | |
|---|---|---|
| 0564924A2 | 5/1992 | European Pat. Off. . |
| WO9204370 | 3/1992 | WIPO . |
| WO9219593 | 11/1992 | WIPO . |
| WO9219745 | 11/1992 | WIPO . |
| WO9221313 | 12/1992 | WIPO . |
| WO9307269 | 4/1993 | WIPO . |
| WO9323548 | 11/1993 | WIPO . |
| WO9524385 | 9/1995 | WIPO . |
| WO9526337 | 10/1995 | WIPO . |
| WO9535367 | 12/1995 | WIPO . |
| WO9615101 | 5/1996 | WIPO . |
| WO 96/3318 | 10/1996 | WIPO . |
| WO 96/36630 | 11/1996 | WIPO . |
| WO 96/41609 | 12/1996 | WIPO . |
| WO 97/36869 | 10/1997 | WIPO . |

OTHER PUBLICATIONS

Chakraborty, Chemical Abstract, vol. 125:115111, 1996.
Shu, Chemical Abstract, vol. 124:342921, 1996.
Chakraborty, Chemical Abstract, vol. 124:290256, 1996.
Slee, Chemical Abstract, vol. 124:105570, 1995.
Tatlock, Chemical Abstract, vol. 124:86677, 1995.
Teague, Chemical Abstract, vol. 124:29474, 1995.
Stocks, Chemical Abstract, vol. 124:29735, 1995.
Wang, Chemical Abstract, vol. 123:275108, 1995.
Nicolaou, Chemical Abstract, vol. 123:285602, 1995.
Armistead, Chemical Abstract, vol. 123:217939, 1995.
Luengo, Chemical Abstract, vol. 123:187705, 1995.
Furber, Chemical Abstract, vol. 123:47577, 1995.
Chakraborty, Chemical Abstract, vol. 123:74408, 1995.
Wang, Chemical Abstract, vol. 123:74101, 1995.
Smith, Chemical Abstract, vol. 123:55541, 1995.
Baumann, Chemical Abstract, vol. 122:314327, 1995.
Munoz, Chemical Abstract, vol. 122:188156, 1994.
Nelson, Chemical Abstract, vol. 122:80964, 1994.
Caffrey, Chemical Abstract, vol. 123:82999, 1994.
Birkenshaw, Chemical Abstract, vol. 122:187213, 1994.
Hauske, Chemical Abstract, vol. 122:45705, 1994.
Stocks, Chemical Abstract, vol. 121:271263, 1994.
Teague, Chemical Abstract, vol. 121:255492, 1994.
Mashkovskii, Chemical Abstract, vol. 121:212542, 1993.
Ranganathan, Chemical Abstract, vol. 121:205990, 1994.
Wang, Chemical Abstract, vol. 121:170041, 1994.
Baader, Chemical Abstract, vol. 121:102790, 1994.
Luengo, Chemical Abstract, vol. 121:49600, 1994.
Holt, Chemical Abstract, vol. 121:224, 1994.
Teague, Chemical Abstract, vol. 121:215, 1993.
Karle, Chemical Abstract, vol. 120:324190, 1994.
Skotnicki, Chemical Abstract, vol. 120:323021, 1994.
Skotnicki, Chemical Abstract, vol. 120:323020, 1994.
Holt, Chemical Abstract, vol. 120:323019, 1993.
Rao, Chemical Abstract, vol. 120:323003, 1993.
Yamashita, Chemical Abstract, vol. 120:315168, 1994.
Andrus, Chemical Abstract, vol. 120:134101, 1993.
Holt, Chemical Abstract, vol. 120:134099, 1993.
Luengo, Chemical Abstract, vol. 120:54365, 1993.
Steffan, Chemical Abstract, vol. 120:54360, 1993.
Nicolaou, Chemical Abstract, vol. 119:278059, 1993.
Hayward, Chemical Abstract, vol. 119:249751, 1993.
Pattenden, Chemical Abstract, vol. 119:95189, 1993.
Yohannes, Chemical Abstract, vol. 119:49108, 1993.
Furber, Chemical Abstract, vol. 119:27877, 1993.
Luengo, Chemical Abstract, vol. 118:233723, 1993.
Ranganathan, Chemical Abstract, vol. 118:213513, 1993.
Yohannes, Chemical Abstract, vol. 118:147360, 1992.
Hauske, Chemical Abstract, vol. 118:22591, 1992.
Cunliffe, Chemical Abstract, vol. 117:49183, 1992.
Goulet, Chemical Abstract, vol. 116:193989, 1991.
Waldmann, Chemical Abstract, vol. 116:41997, 1991.
Goulet, Chemical Abstract, vol. 115:255882, 1991.
Krit, Chemical Abstract, vol. 115:232847, 1991.
Rao, Chemical Abstract, vol. 114:247016, 1991.
Fisher, Chemical Abstract, vol. 114:228608, 1991.
Linde, Chemical Abstract, vol. 114:206955, 1991.

(List continued on next page.)

Primary Examiner—Alan L. Rotman
Assistant Examiner—D. Margaret M. Mach
Attorney, Agent, or Firm—Gary M. Nath; Todd L. Juneau; Nath & Associates

[57] ABSTRACT

This invention relates to neurotrophic low molecular weight, small molecule N-oxides of heterocyclic esters, amides, thioesters, and ketones having an affinity for FKBP-type immunophilins, and their use as inhibitors of the enzyme activity associated with immunophilin proteins, particularly peptidyl-prolyl isomerase, or rotamase, enzyme activity.

20 Claims, 1 Drawing Sheet

OTHER PUBLICATIONS

Dragovich et al., "Structured–Based Design of Novel, Urea–Containing FKBP12 Inhibitors," *J. Med. Chem.*, 1996, 39, 1872–1884.

Gold et al., The Immunosuppressant FK506 Increases the Rate of Axonal Regeneration in Rate Sciatic Nerve, The Journal of Neuroscience, 1995, 15(11), 7509–7516.

Gold et al, "The Immunosuppressant FK506 increases functional recovery and nerve regeneration following peripheral nerve injury," Restorative Neurology and Neuroscience, 1994, 6, 287–296.

Lyons et al., "Immunosuppressant FK506 promotes neurite outgrowth in culture of PC12 cells and sensory ganglia," Proc. Natl. Acad. Sci. USA, 1994, 91, 3191–3195.

Gold, et al, "Multiple signals underlie the anatomy–induced up–regulation of c–JUN in adult sensory neurons," Neuroscience Letters 176, 1994, 123–127.

Gold et al., "Regulation of the transcription factor c–JUN by nerve growth factor in adult sensory neurons," Neuroscience Letters 154, 1993, 129–133.

Sharkey et al., Chemical Abstracts, 121:221398, 1994.

Kelly et al., Chemical Abstracts, 122:114965, 1994.

Hauske, James R. et al., "Design and Synthesis of Novel FKBP Inhibitors," *J. Med. Chem.*, 1992, 35, pp. 4284–4296.

Holt, Dennis A. et al., "Structure–Activity Studies of Non-macrocyclic Rapamycin Derivatives," *Bioorganic & Medical Chemistry Letters*, 1993, vol. 3, No. 10, pp. 1977–1980.

Yamashita, Dennis S. et al. "Design Synthesis and Evaluuation of Dual Domain FKBP Ligands," *Bioorganic & Medicinal Chemistry Letters*, 1994, vol. 4, No. 2 pp. 325–328.

Luengo, Juan I. et al. "Synthesis and Structure–Activity Relationships of Macrocyclic FKBP Ligands," *Bioorganic & Medicinal Chemistry Letters*, 1994, vol. 4, No. 2, pp. 321–324.

Holt, Dennis A. et al. "Structure–Activity Studies of Synthetic FKBP Ligands as Peptidyl–Prolyl Isomerase Inhibitors," *Bioorganic & Medicinal Chemistry Letters*, 1994, vol. 4, No. 2, pp. 315–320.

Caffrey, Moya V. et al. "Synthesis and Evaluation of Dual Domain Macrocyclic FKBP12 Ligands," *Bioorganic & Medicinal Chemistry Letters*, 1994, vol. 4, No. 21, pp. 2507–2510.

Birkenshaw, Timothy N. et al. "Synthetic FKBP12 Ligands. Design and Synthesis of Pyranose Replacements," *Bioorganic & Medicinal Chemistry Letters*, 1994, vol. 4, No. 21, pp. 2501–2506.

Holt, Dennis A. et al. "Design, Synthesis, and Kinetic Evaluation of High–Affinity FKBP Ligands and the X–ray Crystal Structures of Their Complexes with FKBP12," *J. Am. Chem. Soc.*, 1993, 115, pp. 9925–9938.

Wang, Gary T. et al. "Synthesis and FKBP Binding of Small Molecule Mimics of the Tricarbonyl Region of FK506," *Bioorganic & Medicinal Chemistry Letters*, 1994, vol. 4, No. 9, pp. 1161–1166.

Snyder, Solomon H. and Sabatini David M., "Immunophilins and the Nervous System," *Nature Medicine*, 1995, vol. 1, No. 1, pp. 32–37.

N-OXIDES OF HETEROCYCLIC ESTERS, AMIDES, THIOESTERS, AND KETONES

BACKGROUND OF THE INVENTION

1. Field of Invention

This invention relates to neurotrophic low molecular weight, small molecule N-oxides of heterocyclic esters having an affinity for FKBP-type immunophilins, and their use as inhibitors of the enzyme activity associated with immunophilin proteins, particularly peptidyl-prolyl isomerase, or rotamase, enzyme activity.

2. Description of Related Art

The term immunophilin refers to a number of proteins that serve as receptors for the principal immunosuppressant drugs, cyclosporin A (CsA), FK506 and rapamycin. Known classes of immunophilins are cyclophilins and FK506 binding proteins, or FKBPs. Cyclosporin A binds to cyclophilin A while FK506 and rapamycin bind to FKBP12. These immunophilin-drug complexes interface with various intracellular signal transduction systems, especially the immune and nervous systems.

Immunophilins are known to have peptidyl-prolyl isomerase (PPIase), or rotamase, enzyme activity. It has been determined that rotamase enzyme activity plays a role in the catalyzation of the interconversion of the cis and trans isomers of peptide and protein substrates for the immunophilin proteins.

Immunophilins were originally discovered and studied in the immune tissue. It was initially postulated by those skilled in the art that inhibition of the immunophilins' rotamase activity leads to inhibition of T-cell proliferation, thereby causing the immunosuppressive activity exhibited by immunosuppressant drugs, such as cyclosporin A, FK506 and rapamycin. Further study has shown that the inhibition of rotamase activity, in and of itself, does not result in immunosuppressive activity. Schreiber et al., *Science*, 1990, vol. 250, pp. 556–559. Instead, immunosuppression appears to stem from the formulation of a complex of immunosuppressant drugs and immunophilins. It has been shown that the immunophilin-drug complexes interact with ternary protein targets as their mode of action. Schreiber et al., *Cell*, 1991, vol. 66, pp. 807–815. In the case of FKBP-FK506 and cyclophilin-CsA, the immunophilin-drug complexes bind to the enzyme calcineurin and inhibit the T-cell receptor signalling which leads to T-cell proliferation. Similarly, the immunophilin-drug complex of FKBP-rapamycin interacts with the RAFT1/FRAP protein and inhibits the IL-2 receptor signalling.

Immunophilins have been found to be present at high concentrations in the central nervous system. Immunophilins are enriched 10–50 times more in the central nervous system than in the immune system. Within neural tissues, immunophilins appear to influence nitric oxide synthesis, neurotransmitter release and neuronal process extension.

It has been found that picomolar concentrations of an immunosuppressant such as FK506 and rapamycin stimulate neurite outgrowth in PC12 cells and sensory neurons, namely dorsal root ganglion cells (DRGs). Lyons et al., *Proc. of Natl. Acad. Sci.*, 1994, vol. 91, pp. 3191–3195. In whole animal experiments, FK506 has been shown to stimulate nerve regeneration following facial nerve injury.

Surprisingly, it has been found that certain compounds with a high affinity for FKBPs are potent rotamase inhibitors and exhibit excellent neurotrophic effects. Furthermore, these rotamase inhibitors are devoid of immunosuppressive activity. These findings suggest the use of rotamase inhibitors in treating various peripheral neuropathies and enhancing neuronal regrowth in the central nervous system (CNS). Studies have demonstrated that neurodegenerative disorders such as Alzheimer's disease, Parkinson's disease, and amyotrophic lateral sclerosis (ALS) may occur due to the loss, or decreased availability, of a neurotrophic substance specific for a particular population of neurons affected in the disorder.

Several neurotrophic factors affecting specific neuronal populations in the central nervous system have been identified. For example, it has been hypothesized that Alzheimer's disease results from a decrease or loss of nerve growth factor (NGF). It has thus been proposed to treat Senile Dementia Alzheimer's Type (SDAT) patients with exogenous nerve growth factor or other neurotrophic proteins, such as brain derived growth factor, glial derived growth factor, ciliary neurotrophic factor and neurotropin-3, to increase the survival of degenerating neuronal populations.

Clinical application of these proteins in various neurological disease states is hampered by difficulties in the delivery and bioavailability of large proteins to nervous system targets. By contrast, immunosuppressant drugs with neurotrophic activity are relatively small and display excellent bioavailability and specificity. However, when administered chronically, immunosuppressant drugs exhibit a number of potentially serious side effects including nephrotoxicity, such as impairment of glomerular filtration and irreversible interstitial fibrosis (Kopp et al., *J. Am. Soc. Nephrol.*, 1991, 1:162); neurological deficits, such as involuntary tremors, or non-specific cerebral angina, such as non-localized headaches (De Groen et al., *N. Engl. J. Med.*, 1987, 317:861); and vascular hypertension with complications resulting therefrom (Kahan et al., *N. Engl. J. Med.*, 1989, 321:1725).

In order to prevent the side effects associated with use of the immunosuppressant compounds, the present invention provides non-immunosuppressive compounds containing small molecule FKBP rotamase inhibitors for enhancing neurite outgrowth, and promoting neuronal growth and regeneration in various neuropathological situations where neuronal repair can be facilitated, including: peripheral nerve damage caused by physical injury or disease state such as diabetes; physical damage to the central nervous system (spinal cord and brain); brain damage associated with stroke; and neurological disorders relating to neurodegeneration, such as Parkinson's disease, SDAT (Alzheimer's disease), and amyotrophic lateral sclerosis.

SUMMARY OF THE INVENTION

The present invention relates to neurotrophic low molecular weight, small molecule compounds having an affinity for FKBP-type immunophilins. Once bound to these proteins, the neurotrophic compounds are potent inhibitors of the enzyme activity associated with immunophilin proteins, particularly peptidyl-prolyl isomerase, or rotamase, enzyme activity. A key feature of the compounds of the present invention is that they do not exert any significant immunosuppressive activity in addition to their neurotrophic activity. Another significant feature is the novel addition of the oxidation of specific amine groups to the corresponding N-oxide to provide an unexpected increase in bioavailability and potency as compared to compounds lacking the N-oxide group.

Specifically, the present invention relates to a compound of formula I:

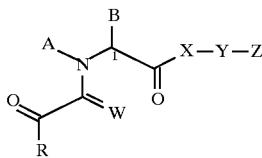

or a pharmaceutically acceptable salt thereof, wherein:

A and B are taken together, with the nitrogen and carbon atoms to which they are respectively attached, to form a 5–7 membered saturated or unsaturated heterocyclic ring containing any combination of $CH_2$, O, S, SO, $SO_2$, NH or $NR_1$ in any chemically stable oxidation state;

W is O, S, $CH_2$, or $H_2$;

R is a $C_1$–$C_6$ straight or branched chain alkyl or alkenyl group optionally substituted with $C_3$–$C_8$ cycloalkyl, $C_3$ or $C_5$ cycloalkyl, $C_5$–$C_7$ cycloalkenyl, or $Ar_1$, where said alkyl, alkenyl, cycloalkyl, or cycloalkenyl groups may be optionally substituted with $C_1$–$C_4$ alkyl, $C_1$–$C_4$ alkenyl, or hydroxy, and where $Ar_1$ is selected from the group consisting of 1-napthyl, 2-napthyl, 1-indolyl, 2-indolyl, 2-furyl, 3-furyl, 2-thienyl, 3-thienyl, 2-pyridyl, 3-pyridyl, 4-pyridyl, or phenyl, having one to three substituents which are independently selected from the group consisting of hyrogen, halo, hydroxyl, nitro, trifluoromethyl, $C_1$–$C_6$ straight or branched alkyl or alkenyl, $C_1$–$C_4$ alkenyloxy, phenoxy, benzyloxy, and amino;

X is O, NH, $NR_1$, S, CH, $CR_1$, or $C(R_1)_2$;

Y is a direct bond, or a $C_1$–$C_6$ straight or branched chain alkyl or alkenyl which is optionally substituted in one or more positions with $C_1$–$C_6$ straight or branched chain alkyl or alkenyl, or $C_3$–$C_8$ cycloalkyl, or $C_5$–$C_7$ cycloalkenyl, or hydroxyl, or carbonyl oxygen, or with Ar, where said alkyl, alkenyl, cycloalkyl, cycloalkenyl, or Ar group is optionally substituted with $C_1$–$C_4$ alkyl, $C_1$–$C_4$ alkenyl, or hydroxy, or carbonyl oxygen, or wherein any of the carbon atoms of said alkyl, alkenyl, cycloalkyl, cycloalkenyl, or Ar group is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group; and Z is an aromatic or tertiary alkyl amine oxidized to a corresponding N-oxide, wherein the aromatic amine is Ar oxidized to a corresponding N-oxide where Ar is a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; wherein the heterocyclic ring contains 1–6 heteroatom(s) selected from the group consisting of O, N, S, and a combination thereof wherein at least one of the heteroatoms is N, and wherein the alkyl amine is oxidized to a corresponding N-oxide where alkyl is a $C_1$–$C_6$ straight or branched chain alkyl or alkenyl which is optionally substituted in one or more positions with $C_1$–$C_6$ straight or branched chain alkyl or alkenyl, or $C_3$–$C_8$ cycloalkyl, or $C_5$–$C_7$ cycloalkenyl, or hydroxyl, or carbonyl oxygen, or with Ar, where said alkyl, alkenyl, cycloalkyl, cycloalkenyl, or Ar group is optionally substituted with $C_1$–$C_4$ alkyl, $C_1$–$C_4$ alkenyl, or hydroxy, or carbonyl oxygen, or wherein any of the carbon atoms of said alkyl, alkenyl, cycloalkyl, cycloalkenyl, or Ar group is optionally replaced with O, NH, $NR_1$, S, SO, or $SO_2$; and, $R_1$ is hydrogen, ($C_1$–$C_4$)-straight or branched chain alkyl, ($C_3$–$C_4$)-straight or branched chain alkenyl or alkynyl, or $R_1$ is Y—Z, as defined above.

Another preferred embodiment of this invention is a compound of formula II:

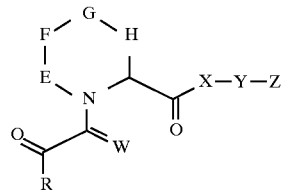

or a pharmaceutically acceptable salt thereof, wherein:

E, F, G and H are independently $CH_2$, O, S, SO, $SO_2$, NH or $NR_1$;

W is O, S, $CH_2$, or $H_2$;

R is a $C_1$–$C_6$ straight or branched chain alkyl or alkenyl group optionally substituted with $C_3$–$C_8$ cycloalkyl, $C_3$ or $C_5$ cycloalkyl, $C_5$–$C_7$ cycloalkenyl, or $Ar_1$, where said alkyl, alkenyl, cycloalkyl, or cycloalkenyl groups may be optionally substituted with $C_1$–$C_4$ alkyl, $C_1$–$C_4$ alkenyl, or hydroxy, and where $Ar_1$ is selected from the group consisting of 1-napthyl, 2-napthyl, 1-indolyl, 2-indolyl, 2-furyl, 3-furyl, 2-thienyl, 3-thienyl, 2-pyridyl, 3-pyridyl, 4-pyridyl, or phenyl, having one to three substituents which are independently selected from the group consisting of hyrogen, halo, hydroxyl, nitro, trifluoromethyl, $C_1$–$C_6$ straight or branched alkyl or alkenyl, $C_1$–$C_4$ alkenyloxy, phenoxy, benzyloxy, and amino;

X is O, NH, $NR_1$, S, CH, $CR_1$, or $C(R_1)_2$;

Y is a direct bond, or a $C_1$–$C_6$ straight or branched chain alkyl or alkenyl which is optionally substituted in one or more positions with $C_1$–$C_6$ straight or branched chain alkyl or alkenyl, or $C_3$–$C_8$ cycloalkyl, or $C_5$–$C_7$ cycloalkenyl, or hydroxyl, or carbonyl oxygen, or with Ar, where said alkyl, alkenyl, cycloalkyl, cycloalkenyl, or Ar group is optionally substituted with $C_1$–$C_4$ alkyl, $C_1$–$C_4$ alkenyl, or hydroxy, or carbonyl oxygen, or wherein any of the carbon atoms of said alkyl, alkenyl, cycloalkyl, cycloalkenyl, or Ar group is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group; and Z is an aromatic or tertiary alkyl amine oxidized to a corresponding N-oxide, wherein the aromatic amine is Ar oxidized to a corresponding N-oxide where Ar is a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; wherein the heterocyclic ring contains 1–6 heteroatom(s) selected from the group consisting of O, N, S, and a combination thereof wherein at least one of the heteroatoms is N, and wherein the alkyl amine is oxidized to a corresponding N-oxide where alkyl is a $C_1$–$C_6$ straight or branched chain alkyl or alkenyl which is optionally substituted in one or more positions with $C_1$–$C_6$ straight or branched chain alkyl or alkenyl, or $C_3$–$C_8$ cycloalkyl, or $C_5$–$C_7$cycloalkenyl, or hydroxyl, or carbonyl oxygen, or with Ar, where said alkyl, alkenyl, cycloalkyl, cycloalkenyl, or Ar group is optionally substituted with $C_1$–$C_4$ alkyl, $C_1$–$C_4$ alkenyl, or hydroxy, or carbonyl oxygen, or wherein any of the carbon atoms of said alkyl, alkenyl, cycloalkyl, cycloalkenyl, or Ar group is optionally replaced with O, NH, $NR_1$, S, SO, or $SO_2$; and, $R_1$ is hydrogen, ($C_1$–$C_4$)-straight or branched chain alkyl, ($C_3$–$C_4$)-straight or branched chain alkenyl or alkynyl, or $R_1$ is Y—Z, as defined above.

Another preferred embodiment is a compound of formula III:

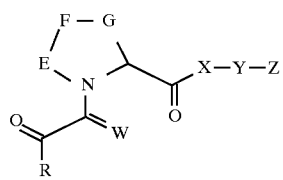

or a pharmaceutically acceptable salt thereof, wherein:

E, F, and G are independently $CH_2$, O, S, SO, $SO_2$, NH or $NR_1$;

W is O, S, $CH_2$, or $H_2$;

R is a $C_1$–$C_6$ straight or branched chain alkyl or alkenyl group optionally substituted with $C_3$–$C_8$ cycloalkyl, $C_3$ or $C_5$ cycloalkyl, $C_5$–$C_7$ cycloalkenyl, or $Ar_1$, where said alkyl, alkenyl, cycloalkyl, or cycloalkenyl groups may be optionally substituted with $C_1$–$C_4$ alkyl, $C_1$–$C_4$ alkenyl, or hydroxy, and where $Ar_1$ is selected from the group consisting of 1-napthyl, 2-napthyl, 1-indolyl, 2-indolyl, 2-furyl, 3-furyl, 2-thienyl, 3-thienyl, 2-pyridyl, 3-pyridyl, 4-pyridyl, or phenyl, having one to three substituents which are independently selected from the group consisting of hyrogen, halo, hydroxyl, nitro, trifluoromethyl, $C_1$–$C_6$ straight or branched alkyl or alkenyl, $C_1$–$C_4$ alkenyloxy, phenoxy, benzyloxy, and amino;

X is O, NH, $NR_1$, S, CH, $CR_1$, or $C(R_1)_2$;

Y is a direct bond, or a C1–$C_6$ straight or branched chain alkyl or alkenyl which is optionally substituted in one or more positions with $C_1$–$C_6$ straight or branched chain alkyl or alkenyl, or $C_3$–$C_8$ cycloalkyl, or $C_5$–$C_7$ cycloalkenyl, or hydroxyl, or carbonyl oxygen, or with Ar, where said alkyl, alkenyl, cycloalkyl, cycloalkenyl, or Ar group is optionally substituted with $C_1$–$C_4$ alkyl, $C_1$–$C_4$ alkenyl, or hydroxy, or carbonyl oxygen, or wherein any of the carbon atoms of said alkyl, alkenyl, cycloalkyl, cycloalkenyl, or Ar group is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group; and Z is an aromatic or tertiary alkyl amine oxidized to a corresponding N-oxide, wherein the aromatic amine is Ar oxidized to a corresponding N-oxide where Ar is a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; wherein the heterocyclic ring contains 1–6 heteroatom(s) selected from the group consisting of O, N, S, and a combination thereof wherein at least one of the heteroatoms is N, and wherein the alkyl amine is oxidized to a corresponding N-oxide where alkyl is a $C_1$–$C_6$ straight or branched chain alkyl or alkenyl which is optionally substituted in one or more positions with $C_1$–$C_6$ straight or branched chain alkyl or alkenyl, or $C_3$–$C_8$ cycloalkyl, or $C_5$–$C_7$ cycloalkenyl, or hydroxyl, or carbonyl oxygen, or with Ar, where said alkyl, alkenyl, cycloalkyl, cycloalkenyl, or Ar group is optionally substituted with $C_1$–$C_4$ alkyl, $C_1$–$C_4$ alkenyl, or hydroxy, or carbonyl oxygen, or wherein any of the carbon atoms of said alkyl, alkenyl, cycloalkyl, cycloalkenyl, or Ar group is optionally replaced with O, NH, $NR_1$, S, SO, or $SO_2$; and, $R_1$ is hydrogen, ($C_1$–$C_4$)-straight or branched chain alkyl, ($C_3$–$C_4$)-straight or branched chain alkenyl or alkynyl, or $R_1$ is Y—Z, as defined above.

A further particularly preferred embodiment of this invention is a compound of formula IV:

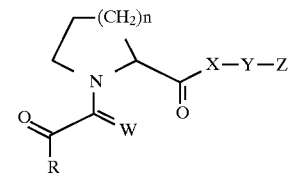

or a pharmaceutically acceptable salt thereof, wherein:

n is 1, 2 or 3 forming a 5–7 member heterocyclic ring;

W is O, S, $CH_2$, or $H_2$;

R is a $C_1$–$C_6$ straight or branched chain alkyl or alkenyl group optionally substituted with $C_3$–$C_8$ cycloalkyl, $C_3$ or $C_5$ cycloalkyl, $C_5$–$C_7$ cycloalkenyl, or $Ar_1$, where said alkyl, alkenyl, cycloalkyl, or cycloalkenyl groups may be optionally substituted with $C_1$–$C_4$ alkyl, $C_1$–$C_4$ alkenyl, or hydroxy, and where $Ar_1$ is selected from the group consisting of 1-napthyl, 2-napthyl, 1-indolyl, 2-indolyl, 2-furyl, 3-furyl, 2-thienyl, 3-thienyl, 2-pyridyl, 3-pyridyl, 4-pyridyl, or phenyl, having one to three substituents which are independently selected from the group consisting of hyrogen, halo, hydroxyl, nitro, trifluoromethyl, $C_1$–$C_6$ straight or branched alkyl or alkenyl, $C_1$–$C_4$ alkenyloxy, phenoxy, benzyloxy, and amino;

X is O, NH, $NR_1$, S, CH, $CR_1$, or $C(R_1)_2$;

Y is a direct bond, or a C1–$C_6$ straight or branched chain alkyl or alkenyl which is optionally substituted in one or more positions with $C_1$–$C_6$ straight or branched chain alkyl or alkenyl, or $C_3$–$C_8$ cycloalkyl, or $C_5$–$C_7$ cycloalkenyl, or hydroxyl, or carbonyl oxygen, or with Ar, where said alkyl, alkenyl, cycloalkyl, cycloalkenyl, or Ar group is optionally substituted with $C_1$–$C_4$ alkyl, $C_1$–$C_4$ alkenyl, or hydroxy, or carbonyl oxygen, or wherein any of the carbon atoms of said alkyl, alkenyl, cycloalkyl, cycloalkenyl, or Ar group is optionally replaced with O, NH, NR$_2$, S, SO, or SO$_2$, where R$_2$ is selected from the group consisting of hydrogen, (C$_1$–C$_4$)-straight or branched chain alkyl, (C$_3$–C$_4$)-straight or branched chain alkenyl or alkynyl, and (C$_1$–C$_4$) bridging alkyl wherein a bridge is formed between the nitrogen and a carbon atom of said alkyl or alkenyl chain containing said heteroatom to form a ring, wherein said ring is optionally fused to an Ar group; and Z is an aromatic or tertiary alkyl amine oxidized to a corresponding N-oxide, wherein the aromatic amine is Ar oxidized to a corresponding N-oxide where Ar is a mono-, bi- or tricyclic, carbo- or heterocyclic ring, wherein the ring is either unsubstituted or substituted in one to three position (s) with halo, hydroxyl, nitro, trifluoromethyl, C$_1$–C$_6$ straight or branched chain alkyl or alkenyl, C$_1$–C$_4$ alkoxy, C$_1$–C$_4$ alkenyloxy, phenoxy, benzyloxy, amino, or a combination thereof; wherein the individual ring sizes are 5–6 members; wherein the heterocyclic ring contains 1–6 heteroatom(s) selected from the group consisting of O, N, S, and a combination thereof wherein at least one of the heteroatoms is N, and wherein the alkyl amine is oxidized to a corresponding N-oxide where alkyl is a C$_1$–C$_6$ straight or branched chain alkyl or alkenyl which is optionally substituted in one or more positions with C$_1$–C$_6$ straight or branched chain alkyl or alkenyl, or C$_3$–C$_8$ cycloalkyl, or C$_5$–C$_7$ cycloalkenyl, or hydroxyl, or carbonyl oxygen, or with Ar, where said alkyl, alkenyl, cycloalkyl, cycloalkenyl, or Ar group is optionally substituted with C$_1$–C$_4$ alkyl, C$_1$–C$_4$ alkenyl, or hydroxy, or carbonyl oxygen, or wherein any of the carbon atoms of said alkyl, alkenyl, cycloalkyl, cycloalkenyl, or Ar group is optionally replaced with O, NH, NR$_1$, S, SO, or SO$_2$; and, R$_1$ is hydrogen, (C$_1$–C$_4$)-straight or branched chain alkyl, (C$_3$–C$_4$)-straight or branched chain alkenyl or alkynyl, or R$_1$ is Y—Z, as defined above.

In preferred embodiments, Ar is selected from the group consisting of pyrrolidinyl, pyridyl, pyrimidyl, pyrazyl, pyridazyl, quinolinyl, and isoquinolinyl.

Particularly preferred compounds of the present invention include:

3-(2-Pyridyl)-1-propyl(2S)-1-(3,3-Dimethyl-1,2-dioxopentyl)-2-pyrrolidinecarboxylate, N-oxide;

3-(3-Pyridyl)-1-propyl(2S)-1-(3,3-Dimethyl-1,2-dioxopentyl)-2-pyrrolidinecarboxylate, N-oxide;

3-(4-Pyridyl)-1-propyl(2S)-1-(3,3-Dimethyl-1,2-dioxopentyl)-2-pyrrolidinecarboxylate, N-oxide;

3-(2-Quinolyl)-1-propyl(2S)-1-(1,1-Dimethyl-1,2-dioxopentyl)-2-pyrrolidinecarboxylate, N-oxide;

3-(3-Quinolyl)-1-propyl(2S)-1-(1,1-Dimethyl-1,2-dioxopentyl)-2-pyrrolidinecarboxylate, N-oxide; and 3-(4-Quinolyl)-1-propyl(2S)-1-(1,1-Dimethyl-1,2-dioxopentyl)-2-pyrrolidinecarboxylate, N-oxide.

The present invention also relates to a pharmaceutical composition comprising a neurotrophically effective amount of the compound of formula I, II, III, or IV, and a pharmaceutically acceptable carrier.

The present invention further includes methods of using the compounds of the present invention. One preferred embodiment includes a method of stimulating damaged neurons in an animal, comprising:

administering to the animal a neurotrophically effective amount of a compound of the present invention.

Another preferred embodiment of the present invention includes a method of promoting neuronal regeneration in an animal, comprising:

administering to the animal a neurotrophically effective amount of a compound of the present invention.

Yet another embodiment of the present invention includes a method of preventing neurodegeneration in an animal, comprising:

administering to the animal a neurotrophically effective amount of a compound of the present invention.

Another embodiment includes a method of treating neurological disorders in an animal, comprising:

administering to the animal a neurotrophically effective amount of a compound of the present invention.

The neurological disorders for which the compounds of the present invention are particularly useful are selected from the group consisting of: peripheral neuropathy caused by physical injury or disease state, physical damage to the brain, physical damage to the spinal cord, stroke associated with brain damage, and neurological disorder relating to neurodegeneration. Examples of neurological disorders relating to neurodegeneration are Alzheimer's Disease, Parkinson's Disease, and amyotrophic lateral sclerosis.

BRIEF DESCRIPTION OF THE INVENTION

FIG. 1 is a bar graph showing Protection of Striatal TH Innervation Density from MPTP-toxicity by Concurrent Drug Dosing. FIG. 1 shows that at administration of 4 mg/kg of the compounds of the present invention there is a remarkable protection of striatal nerves from MPTP-toxicity.

DETAILED DESCRIPTION OF THE INVENTION

Definitions

Figure 1:
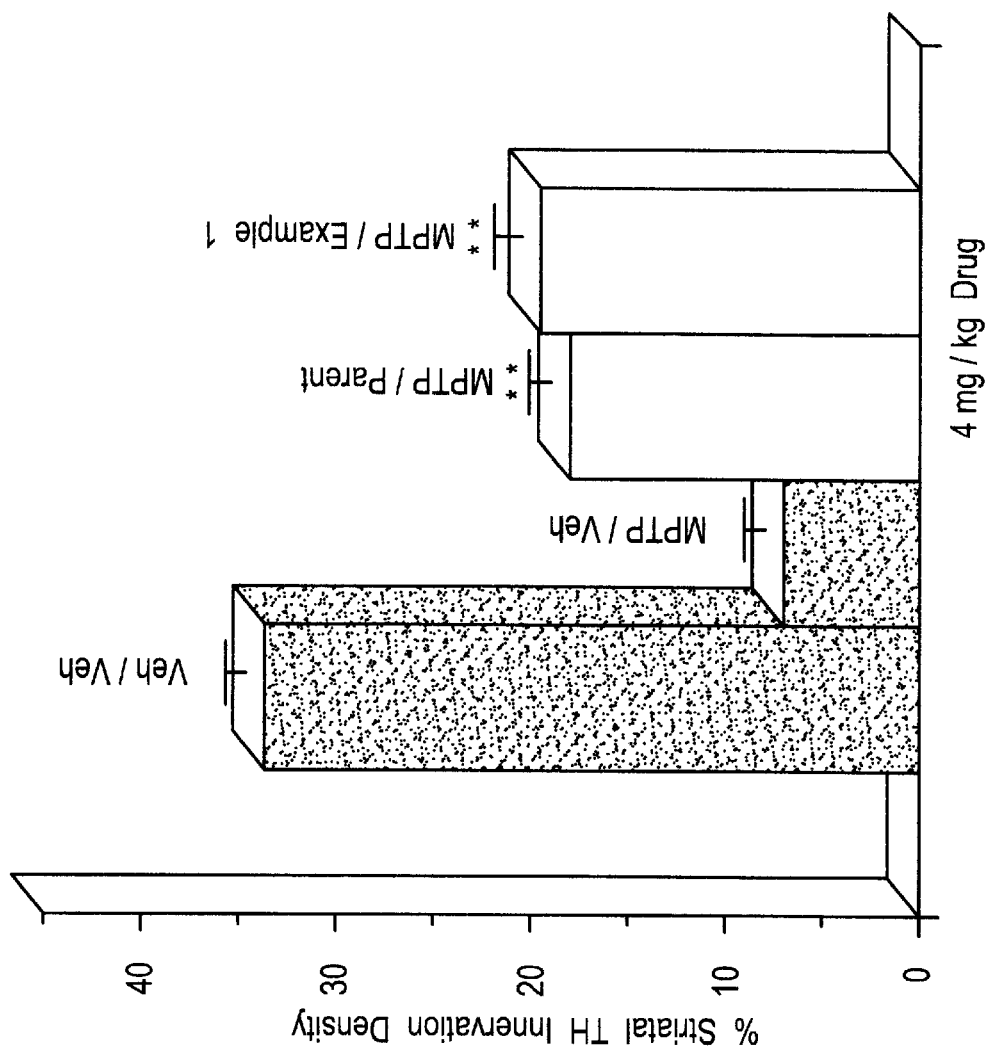

"Alkyl" means a branched or unbranched saturated hydrocarbon chain containing 1 to 6 carbon atoms, such as methyl, ethyl, propyl, iso-propyl, butyl, iso-butyl, tert-butyl, n-pentyl, n-hexyl, and the like, unless otherwise indicated.

"Alkoxy" means the group —OR wherein R is alkyl as herein defined. Preferably, R is a branched or unbranched saturated hydrocarbon chain containing 1 to 3 carbon atoms.

"Halo" means fluoro, chloro, bromo, or iodo, unless otherwise indicated.

"Phenyl" includes all possible isomeric phenyl radicals, optionally monosubstituted or multi-substituted with substituents selected from the group consisting of alkyl, alkoxy, hydroxy, halo, and haloalkyl.

The term "C$_1$–C$_6$" and similar terminology found in standard chemical nomenclature, when used for alkyl and alkenyl chains, is known in the art to include subchains such as C$_1$–C$_3$, C$_1$–C$_4$, C$_1$–C$_5$, C$_1$–C$_6$, C$_2$–C$_4$, C$_2$–C$_5$, C$_2$–C6, C$_3$–C$_5$, C$_3$–C$_6$, C$_4$–C$_6$, and the variants thereof.

The term "pharmaceutically acceptable salt" refers to salts of the subject compounds which posses the desired pharmacological activity and which are neither biologically nor otherwise undesirable. The salts can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The compounds of this invention possess at least one asymmetric center and thus can be produced as mixtures of stereoisomers or as individual enantiomers or diastereomers. The individual stereoisomers may be obtained by using an optically active starting material, by resolving a racemic or non-racemic mixture of an intermediate at some appropriate stage of the synthesis, or by resolution of the compound of formula (I). It is understood that the individual stereoisomers as well as mixtures (racemic and non-racemic) of stereoisomers are encompassed by the scope of the present invention. The S-stereoisomer at atom 1 of formula I is most preferred due to its greater activity.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other.

"Diastereoisomers" are stereoisomers which are not mirror images of each other.

"Racemic mixture" means a mixture containing equal parts of individual enantiomers. "Non-racemic mixture" is a mixture containing unequal parts of individual enantiomers or stereoisomers.

The term "treatment" as used herein covers any treatment of a disease and/or condition in an animal, particularly a human, and includes:

(i) preventing a disease and/or condition from occurring in a subject which may be predisposed to the disease and/or condition but has not yet been diagnosed as having it;

(ii) inhibiting the disease and/or condition, i.e., arresting its development; or (iii) relieving the disease and/or condition, i.e., causing regression of the disease and/or condition.

The term "effecting" as directed to "effecting neuronal activity" relates to producing or bringing about a desired effect or result and includes without limitaion stimulating neurons, promoting regeneration preventing degeneration, protecting from degeneration and treating disorders.

The system used in naming the compounds of the present invention is shown below, using a compound of formula IV as an example.

A compound of the present invention, especially Formula IV, wherein n is 1, R is 1,1-dimethylpentyl, X is O, Y is $(CH_2)_3$, and Z is 3-pyridyl-N-oxide, is named 3-(3-Pyridyl)-1-propyl(2S)-1-(3,3-Dimethyl-1,2-dioxopentyl)-2-pyrrolidinecarboxylate, N-oxide.

Compounds of the Invention

The neurotrophic low molecular weight, small molecule FKBP inhibitor compounds of this invention have an affinity for FKBP-type immunophilins, such as FKBP12. When the neurotrophic compounds of this invention are bound to an FKBP-type immunophilin, they have been found to inhibit the prolyl-peptidyl cis-trans isomerase activity, or rotamase, activity of the binding protein and unexpectedly stimulate neurite growth.

Specific exemplifications of these embodiments are presented in TABLE I.

TABLE I

| No. | n | X | Y | Z | R |
|---|---|---|---|---|---|
| 1 | 1 | O | $(CH_2)_3$ | 3-Pyridyl N-oxide | 1,1-dimethylpentyl |
| 2 | 1 | O | $(CH_2)_3$ | 2-Pyridyl N-oxide | 1,1-dimethylpentyl |
| 3 | 1 | O | $(CH_2)_3$ | 4-Pyridyl N-oxide | 1,1-dimethylpentyl |
| 4 | 1 | O | $(CH_2)_3$ | 2-Quinolyl N-oxide | 1,1-dimethylpentyl |
| 5 | 1 | O | $(CH_2)_3$ | 3-Quinolyl N-oxide | 1,1-dimethylpentyl |
| 6 | 1 | O | $(CH_2)_3$ | 4-Quinolyl N-oxide | 1,1-dimethylpentyl |

The most preferred compounds of formula IV are:

3-(2-Pyridyl)-1-propyl(2S)-1-(3,3-Dimethyl-1,2-dioxopentyl)-2-pyrrolidinecarboxylate, N-oxide;

3-(3-Pyridyl)-1-propyl(2S)-1-(3,3-Dimethyl-1,2-dioxopentyl)-2-pyrrolidinecarboxylate, N-oxide;

3-(4-Pyridyl)-1-propyl(2S)-1-(3,3-Dimethyl-1,2-dioxopentyl)-2-pyrrolidinecarboxylate, N-oxide;

3-(2-Quinolyl)-1-propyl(2S)-1-(1,1-Dimethyl-1,2-dioxopentyl)-2-pyrrolidinecarboxylate, N-oxide;

3-(3-Quinolyl)-1-propyl(2S)-1-(1,1-Dimethyl-1,2-dioxopentyl)-2-pyrrolidinecarboxylate, N-oxide; and 3-(4-Quinolyl)-1-propyl(2S)-1-(1,1-Dimethyl-1,2-dioxopentyl)-2-pyrrolidinecarboxylate, N-oxide.

The compounds of the present invention exist as stereoisomeric forms, either enantiomers or diastereoisomers. Included within the scope of the invention are the enantiomers, the racemic form, and diastereoisomeric mixtures. Enantiomers and diastereoisomers can be separated by methods known to those skilled in the art.

Methods of Using the Compounds of the Invention

The compounds of the present invention have an affinity for the FK506 binding protein, particularly FKBP12, which is present in the neuronal tissue. When the inventive compounds bind to FKBP in neuronal tissue, they exhibit excellent neurotrophic activity. This activity is useful in the stimulation of damaged neurons, the promotion of neuronal regeneration, the prevention of neurodegeneration, the protection of nerves from neurodegeneration, and the treatment of several neurological disorders known to be associated with neuronal degeneration and peripheral neuropathies.

For the foregoing reasons, the present invention further relates to a method of effecting a neuronal activity in an animal, comprising:

administering to the animal a neurotrophically effective amount of a compound of formula I, II, III or IV.

In a preferred embodiment, the neuronal activity is selected from the group consisting of stimulation of damaged neurons, promotion of neuronal regeneration, prevention of neurodegeneration, protection of neurodegeneration, and treatment of neurological disorder.

The neurological disorders that may be treated include but are not limited to: trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated; ruptured or prolapsed invertebrate disk syndromes; cervical spondylosis; plexus disorders; thoracic outlet destruction syndromes; peripheral neuropathic such as those caused by lead, dapsone, ticks, porphyria, or Guillain-Barré syndrome; Alzheimer's disease; and Parkinson's disease.

The compounds of the present invention are particularly useful for treating a neurological disorder selected from the group consisting of: peripheral neuropathy caused by physical injury or disease state, physical damage to the brain, physical damage to the spinal cord, stroke associated with brain damage, and neurological disorder relating to neurodegeneration. Examples of neurological disorders relating to neurodegeneration are Alzheimer's Disease, Parkinson's Disease, and amyotrophic lateral sclerosis.

Pharmaceutical Compositions and Formulations

For these purposes the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques.

To be effective therapeutically as central nervous system targets, the compounds of the present invention should readily penetrate the blood-brain barrier when peripherally administered. Compounds which cannot penetrate the blood-brain barrier can be effectively administered by an intraventricular route or other appropriate delivery system suitable for administration to the brain.

The compounds of the present invention may be administered in the form of sterile injectable preparations, for example, as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile, fixed oils are conventionally employed as solvents or suspending mediums. For this purpose, any bland fixed oil may be employed including synthetic mono- or di-glycerides. Fatty acids such as oleic acid and its glyceride derivatives, including olive oil and castor oil, especially in their polyoxyethylated versions, are useful in the preparation of injectables. These oil solutions or suspensions may also contain long-chain alcohol diluents or dispersants.

The compounds may be administered orally in the form of capsules, tablets, aqueous suspensions or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening and/or flavoring and/or coloring agents.

The compounds of this invention may also be administered rectally in the form of suppositories. These compositions can be prepared by mixing the drug with a suitable non-irritating excipient which is solid at room temperature, but liquid at rectal temperature and, therefore, will melt in the rectum to release the drug. Such materials include cocoa butter, beeswax and polyethylene glycols.

The compounds of this invention may also be administered topically, especially when the conditions addressed for treatment involve areas or organs readily accessible by topical application, including neurological disorders of the eye, the skin, or the lower intestinal tract. Suitable topical formulations are readily prepared for each of these areas.

For topical application to the eye, or ophthalmic use, the compounds can be formulated as micronized suspensions in isotonic, Ph adjusted sterile saline, or, preferably, as solutions in isotonic, Ph adjusted sterile saline, either with or without a preservative such as benzylalkonium chloride. Alternatively for the ophthalmic uses the compounds may be formulated in an ointment such as petrolatum.

For topical application to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal tract an be effected in a rectal suppository formulation (see above) or in a suitable enema formulation.

Dosage levels on the order of about 0.1 mg to about 10,000 mg of the active ingredient compound are useful in the treatment of the above conditions, with preferred levels of about 0.1 mg to about 1,000 mg. The amount of active ingredient that may be combined with the carrier materials to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

The compounds can be administered with other neurotrophic agents such as neurotrophic growth factor (NGF), glial derived growth factor, brain derived growth factor, ciliary neurotrophic factor, and neurotropin-3. The dosage level of other neurotrophic drugs will depend upon the factors previously stated and the neurotrophic effectiveness of the drug combination.

As discussed above, the compounds of the present invention have an affinity for the FK506 binding protein, particularly FKBP12. The inhibition of the prolyl peptidyl cis-trans isomerase activity of FKBP may be measured as an indicator of this affinity.

Ki Test Procedure

Inhibition of the peptidyl-prolyl isomerase (rotamase) activity of the inventive compounds can be evaluated by known methods described in the literature (Harding, et al., *Nature*, 1989, 341:758–760; Holt et al. *J. Am. Chem. Soc.*, 115:9923–9938). These values are obtained as apparent Ki's and are presented in Table II. The cis-trans isomerization of an alanine-proline bond in a model substrate, N-succinyl-Ala-Ala-Pro-Phe-p-nitroanilide, is monitored spectrophotometrically in a chymotrypsin-coupled assay, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent Ki values.

In a plastic cuvette are added 950 mL of ice cold assay buffer (25 mM HEPES, pH 7.8, 100 mM NaCl), 10 mL of FKBP (2.5 mM dithiothreitol), 25 mL of chymotrypsin (50 mg/ml in 1 mM HCL) and 10 mL of test compound at various concentrations in dimethyl sulfoxide. The reaction is initiated by the addition of 5 mL of substrate (succinyl-Ala-Phe-Pro-Phe-para-nitroanilide, 5 mg/mL in 2.35 mM LiCl in trifluoroethanol).

The absorbance at 390 nm versus time is monitored for 90 seconds using a spectrophotometer and the rate constants are determined from the absorbance versus time data files.

The data for these experiments for representative compounds are presented in Table II under the column "Ki".

The neurotrophic effects of the compounds of the present invention can be demonstrated in cellular biological experiments in vitro, as described below.

Chick Dorsal Root Ganglion Cultures and Neurite Growth

Dorsal root ganglia were dissected from chick embryos of ten day gestation. Whole ganglion explants were cultured on thin layer Matrigel-coated 12 well plates with Liebovitz L15 plus high glucose media supplemented with 2 mM glutamine and 10% fetal calf serum, and also containing 10 $\mu$M cytosine $\beta$-D arabinofuranoside (Ara C) at 37° C. in an environment containing 5% $CO_2$. Twenty-four hours later, the DRGs were treated with various immunophilin ligands. Forty-eight hours after drug treatment, the ganglia were visualized under phase contrast or Hoffman Modulation contrast with a Zeiss Axiovert inverted microscope. Photomicrographs of the explants were made, and neurite outgrowth was quantified. Neurites longer than the DRG diameter were counted as positive, with total number of neurites quantitated per each experimental condition. Three to four DRGs are cultured per well, and each treatment was performed in duplicate.

The unexpectedly greater metabolic stability of the N-oxides of the present invention may be demonstrated in vitro assays. In studies to directly asses the rate of metabolism of N-oxides, a mouse liver microsomal assay was used as described below to model first pass metabolism. Data is presented comparing the N-oxide of Example 1 with its parent (unoxidized) compound, showing the N-oxide has a significantly longer half-life than the parent compound. Additionally, studies using purified esterase enzyme (described in detail below) demonstrated that Example 1 undergoes limited de-esterification in vitro during the course of the study whereas the precursor compound (unoxidized parent compound) undergoes significant degradation under the same reaction conditions.

Microsomal Assay

Liver microsomes from various species were purchased from a commercial supplier. The microsomes are characterized prior to shipment. The reaction mixture contained microsomes, 5 $\mu$M $MgCl_2$, 1 mM NADP, 4 mM glucose-6-phosphate (G-6-P), and 1 unit/4 mL glucose-6-phosphate dehydrogenase (G-6-P DH). The final microsomal protein concentration for all studies was 0.2 mg/mL. Incubations were carried out for 1 hour in a shaking water bath (37° C.). The reaction was terminated by removing an aliquot from the reaction mixture and placing it in a tube with an equal volume of acetonitrile and the bioanalytical internal standard. The results of these experiments are presented as compound half-lives ($t_{1/2}$) in Table II.

Esterase Activity

Purified rabbit liver esterase was purchased from Sigma. Five (5) units of enzyme were placed in 2 mL of 0.05M Tris buffer (pH 7.5). Incubations were performed for 2 hours. The reaction was terminated by removing an aliquot from the reaction mixture and placing it in a tube with an equal volume of acetonitrile and the bioanalytical internal standard. The results of these experiments are presented in Table II as rates of enzymatic degradation of the compounds.

The results of these in vitro experiments for 3-(3-Pyridyl)-1-propyl (2S)-1-(3,3-Dimethyl-1,2-dioxopentyl)-2-pyrrolidinecarboxylate ("Parent") are tabulated in Table II.

TABLE II

| Compound | $K_i$ (nM) | $ED_{50}$ (nM) | $t_{1/2}$ (min) | esterase degradation (pmol/min/mg/protein) |
|---|---|---|---|---|
| Parent | 7.5 | 0.05 | 8.1 | 7521 |
| Example 1 | 225 | 2.3 | 42.8 | 367 |

MPTP Model of Parkinson's Disease

The remarkable neurotrophic and neuroregenerative effects of the present inventive compounds can be further demonstrated in an animal model of neurodegenerative disease. MPTP lesioning of dopaminergic neurons in mice is used as an animal model of Parkinson's Disease. Four week old male CD1 white mice are dosed i.p. with 30 mg/kg of MPTP for 5 days. Test compounds (4 mg/kg), or vehicle, are administered s.c. along with the MPTP for 5 days, as well as for an additional five days following cessation of MPTP treatment. At 18 days following MPTP treatment, the animals are sacrificed and the striata dissected and perfusion-fixed. Immunostaining is performed on sagittal and coronal brain sections using anti-tyrosine hydroxylase 1 g to quantitative survival and recovery of dopaminergic neurons. In animals treated MPTP and vehicle, a substantial loss of functional dopaminergic terminals is observed as compared to non-lesioned animals. Lesioned animals receiving test compounds show a significant recovery of TH-stained dopaminergic neurons. This model presents quantitation for the recovery of TH-positive dopaminergic neurons in the striatum of animals receiving of animals receiving the compounds of the present invention. Data for representative control and lesioned animals not receiving the test drugs is also presented against the data from the animals receiving the compounds of the present invention.

Data for the representative control and lesioned animals not receiving test drugs is presented against the Parent compound and Example 1 of the present invention in FIG. 1. It is clear that, although Example 1 is less potent in vitro, it is more potent in this in vivo model of neurodegeneration, due to its unexpectedly better bioavailability and pharmacokinetics.

EXAMPLES

The following examples are illustrative of the present invention and are not intended to be limitations thereon.

Example 1

Synthesis of 3-(3-Pyridyl)-1-propyl(2S)-1-(3,3-Dimethyl-1,2-dioxopentyl)-2-pyrrolidinecarboxylate, N-oxide. (1)

Methyl (2S)-1-(1,2-dioxo-2-methoxyethyl)-2-pyrrolidinecarboxylate. A solution of L-proline methyl ester hydrochloride (3.08 g; 18.60 mmol) in dry methyl chloride was cooled to 0° C. and treated with triethylamine (3.92 g; 38.74 mmol; 2.1 eq). After stirring the formed slurry under a nitrogen atmosphere for 15 min, a solution of methyl oxalyl chloride (3.20 g; 26.12 mmol) in methylene chloride (45 mL) was added dropwise. The resulting mixture was stirred at 0° C. for 1.5 hr. After filtering to remove solids, the organic phase was washed with water, dried over $MgSO_4$ and concentrated. The crude residue was purified on a silica gel column, eluting with 50% ethyl acetate in hexane, to obtain 3.52 g (88%) of the product as a reddish oil. Mixture of cis-trans amide rotamers; data for trans rotamer given. $^1$H NMR ($CDCl_3$): δ 1.93 (dm, 2H); 2.17 (m, 2H); 3.62 (m, 2H); 3.71 (s, 3H); 3.79, 3.84 (s, 3H total); 4.86 (dd, 1H, J=8.4, 3.3).

Methyl(2S)-1-(1,2-dioxo-3,3-dimethylpentyl)-2-pyrrolidinecarboxylate. A solution of methyl (2S)-1-(1,2-dioxo-2-methoxyethyl)-2-pyrrolidinecarboxylate (2.35 g; 10.90 mmol) in 30 mL of tetrahydrofuran (THF) was cooled to −78° C. and treated with 14.2 mL of a 1.0M solution of 1,1-dimethylpropylmagnesium chloride in THF. After stirring the resulting homogeneous mixture at −78° C. for three hours, the mixture was poured into saturated ammonium chloride (100 mL) and extracted into ethyl acetate. The organic phase was washed with water, dried, and concentrated, and the crude material obtained upon removal of the solvent was purified on a silica gel column, eluting with 25% ethyl acetate in hexane, to obtain 2.10 g (75%) of the oxamate as a colorless oil. $^1$H NMR ($CDCl_3$):δ 0.88 (t,3H); 1.22, 1.26 (s,3H each); 1.75 (dm, 2H); 1.87–2.10 (m,3H); 2.23 (m, 1H); 3.54 (m, 2H); 3.76(s, 3H); 4.52(dm, 1H,J=8.4,3.4).

(2S)-1-(1,2-dioxo-3,3-dimethylpentyl)-2-pyrrolidinecarboxylic acid. A mixture of methyl(2S)-1-(1,2-dioxo-3,3-dimethylpentyl-2-pyrrolidinecarboxylate (2.10 g; 8.23 mmol), 1N LiOH (15 mL), and methanol (50 mL) was stirred at 0° C. for 30 min and at room temperature overnight. The mixture was acidified to pH 1 with 1N HCl, diluted with water, and extracted into 100 mL of methylene chloride. The organic extract was washed with brine and concentrated to deliver 1.73 g (87%) of snow-white solid which did not require further purification. $^1$H NMR ($CDCl_3$) :d 0.87(t,3H); 1.22,1.25(s,3H each); 1.77 (dm,2H); 2.02 (m,2H); 2.17 (m,1H); 2.25 (m,1H); 3.53(dd,2H,J=10.4,7.3); 4.55(dd,1H,J=8.6,4.1).

3-(3-Pyridyl)-1-propyl(2S)-1-(3,3-dimethyl-1,2-dioxopentyl)-2-pyrrolidinecarboxylate. A mixture of (2S)-1-(1,2-dioxo-3,3-dimethylpentyl)-2-pyrrolidinecarboxylic acid (4.58 g; 19 mmol), 3-pyridinepropanol (3.91 g; 28.5 mmol), dicyclohexylcarbodiimide (6.27 g; 30.4 mmol), camphorsulphonic acid (1.47 g; 6.33 mmol) and 4-dimethyl aminopyridine (773 mg; 6.33 mmol) in methylene chloride (100 mL) was stirred overnight under a nitrogene atmosphere. The reaction mixture was filtered through Celite to remove solids and concentrate in vacuo. The crude material was triturated with several portions of ether, and the ether portions were filtered through Celite to remove solids and concentrated in vacuo. The concentrated filtrate was purified on a flash column (gradient elution, 25% ethyl acetate in hexane to pure ethyl acetate) to obtain 5.47 g (80%) of GPI 1046 as a colorless oil (partial hydrate). $^1$H NMR ($CDCl_3$, 300 MHz):δ 0.85 (t,3H); 1.23, 1.26 (s,3H each); 1.63–1.89 (m,2H); 1.90–2.30(m,4H); 2.30–2.50(m,1H); 2.72(t,2H); 3.53(m,2H); 4.19(m,2H); 4.53(m,1H); 7.22(m,1H); 7.53(dd, 1H); 8.45. Anal. Calcd. for $C_{20}H_{28}NO_4$-0.25 $H_2O$: C,65.82; H,7.87; N,7.68. Found: C,66.01; H,7.85; N,7.64.

3-(3-Pyridyl)-1-propyl(2S)-1-(3,3-dimethyl-1,2-dioxopentyl)-2-pyrrolidinecarboxylate, N-oxide. A solution of 3-(3-pyridyl)-1-propyl(2S)-1-(3,3-dimethyl-1,2-dioxopentyl)-2-pyrrolidinecarboxylate (190 mg; 0.52 mmol) and m-chloroperbenzoic acid (160 mg of 57%–86% material, 0.53 mmol) was stirred in methylene chloride (20 mL) at room temperature for 3 hrs. The reaction mixture was diluted with methylene chloride and washed twice with 1N NaOH. The organic extract was dried and concentrated and the crude material was chromatographed, eluting with 10% methanol in ethyl acetate, to obtain 130 mg of the compound of Example 1, $^1$H NMR ($CDCl^3$,300 MHz): δ 0.83 (t,3H); 1.21 (s,3H); 1.25 (s,3H); 1.75–2.23 (m,8H); 2.69 (t,2H,J= 7.5); 3.52 (t,2H,J-6.3); 4.17 (dd,2H, J=6.3); 4.51 (m,1H); 7.16–7.22 (m,2H); 8.06–8.11 (m,2H). Anal. Calcd. for $C_{20}H_{28}N_2O_5$-0.75 $H_2O$: C,61.60; H,7.63; N,7.18. Found: C,61.79; H,7.58; N,7.23.

What is claimed is:

1. A compound of the formula

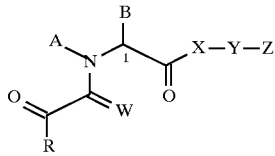

or a pharmaceutically acceptable salt thereof, wherein:

A and B are taken together, with the nitrogen and carbon atoms to which they are respectively attached, to form a 5–7 membered saturated or unsaturated heterocyclic ring having only one heteroatom which is nitrogen, the remaining ring members being carbon, in any chemically stable oxidation state;

W is O, S, $CH_2$, or $H_2$;

R is a $C_1$–$C_6$ straight or branched chain alkyl or alkenyl group optionally substituted with $C_3$–$C_8$ cycloalkyl, $C_3$ or $C_5$ cycloalkyl, $C_5$–$C_7$ cycloalkenyl, or $Ar_1$, where said alkyl, alkenyl, cycloalkyl, or cycloalkenyl groups may be optionally substituted with $C_1$–$C_4$ alkyl, $C_1$–$C_4$ alkenyl, or hydroxy, and where $Ar_1$ is selected from the group consisting of 1-napthyl, 2-napthyl, 1-indolyl, 2-indolyl, 2-furyl, 3-furyl, 2-thienyl, 3-thienyl, 2-pyridyl, 3-pyridyl, 4-pyridyl, or phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkenyloxy, phenoxy, benzyloxy, and amino;

X is O, NH, $NR_1$, S, $CH_2$, $CHR_1$, or $C(R_1)_2$;

Y is a direct bond, or a $C1$–$C_6$ straight or branched chain alkyl or alkenyl which is optionally substituted in one or more positions with $C_1$–$C_6$ straight or branched chain alkyl or alkenyl, or $C_3$–$C_8$ cycloalkyl, or $C_5$–$C_7$ cycloalkenyl, or hydroxyl, or carbonyl oxygen, or with

17

Ar, where said alkyl, alkenyl, cycloalkyl, cycloalkenyl, or Ar group is optionally substituted with $C_1$–$C_4$ alkyl, $C_1$–$C_4$ alkenyl, or hydroxy, or carbonyl oxygen, or wherein any of the carbon atoms of said alkyl, alkenyl, cycloalkyl, cycloalkenyl, or Ar group is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group; and Z is an aromatic or tertiary alkyl amine oxidized to a corresponding N-oxide, wherein the aromatic amine is Ar oxidized to a corresponding N-oxide where Ar is a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; wherein the heterocyclic ring contains 1–6 heteroatom(s) selected from the group consisting of O, N, S, and a combination thereof wherein at least one of the heteroatoms is N, and wherein the alkyl amine is oxidized to a corresponding N-oxide where alkyl is a $C_1$–$C_6$ straight or branched chain alkyl or alkenyl which is optionally substituted in one or more positions with $C_1$–$C_6$ straight or branched chain alkyl or alkenyl, or $C_3$–$C_8$ cycloalkyl, or $C_5$–$C_7$ cycloalkenyl, or hydroxyl, or carbonyl oxygen, or with Ar, where said alkyl, alkenyl, cycloalkyl, cycloalkenyl, or Ar group is optionally substituted with $C_1$–$C_4$ alkyl, $C_1$–$C_4$ alkenyl, or hydroxy, or carbonyl oxygen, or wherein any of the carbon atoms of said alkyl, alkenyl, cycloalkyl, cycloalkenyl, or Ar group is optionally replaced with O, NH, $NR_1$, S, SO, or $SO_2$;

Ar is selected from the group consisting of pyrrolidinyl, pyridyl, pyrimidyl, pyrazyl, pyridazyl, quinolinyl, and isoquinolinyl; and, $R_1$ is hydrogen, ($C_1$–$C_4$)-straight or branched chain alkyl, ($C_3$–$C_4$)-straight or branched chain alkenyl or alkynyl, or $R_1$ is Y—Z as defined above.

2. A pharmaceutical composition comprising a neurotrophically effective amount of the compound of claim 1 and a pharmaceutically acceptable carrier.

3. A method of stimulating the growth of damaged neurons in an animal, comprising:

administering to the animal a neurotrophically effective amount of the compound of claim 1.

4. A method of promoting neuronal regeneration in an animal, comprising:

administering to the animal a neurotrophically effective amount of the compound of claim 1.

5. A compound of formula II comprising:

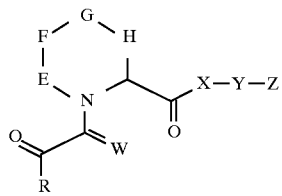

or a pharmaceutically acceptable salt thereof, wherein:

E, F, G and H are independently $CH_2$;

W is O, S, $CH_2$, or $H_2$;

R is a $C_1$–$C_6$ straight or branched chain alkyl or alkenyl group optionally substituted with $C_3$–$C_8$ cycloalkyl, $C_3$ or $C_5$ cycloalkyl, $C_5$–$C_7$ cycloalkenyl, or $Ar_1$, where said alkyl, alkenyl, cycloalkyl, or cycloalkenyl groups may be optionally substituted with $C_1$–$C_4$ alkyl, $C_1$–$C_4$ alkenyl, or hydroxy, and where $Ar_1$ is selected from the group consisting of 1-napthyl, 2-napthyl, 1-indolyl, 2-indolyl, 2-furyl, 3-furyl, 2-thienyl, 3-thienyl, 2-pyridyl, 3-pyridyl, 4-pyridyl, or phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkenyloxy, phenoxy, benzyloxy, and amino;

X is O, NH, $NR_1$, S, $CH_2$, $CHR_1$, or $C(R_1)_2$;

Y is a direct bond, or a $C1$–$C_6$ straight or branched chain alkyl or alkenyl which is optionally substituted in one or more positions with $C_1$–$C_6$ straight or branched chain alkyl or alkenyl, or $C_3$–$C_8$ cycloalkyl, or $C_5$–$C_7$ cycloalkenyl, or hydroxyl, or carbonyl oxygen, or with Ar, where said alkyl, alkenyl, cycloalkyl, cycloalkenyl, or Ar group is optionally substituted with $C_1$–$C_4$ alkyl, $C_1$–$C_4$ alkenyl, or hydroxy, or carbonyl oxygen, or wherein any of the carbon atoms of said alkyl, alkenyl, cycloalkyl, cycloalkenyl, or Ar group is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group; and Z is an aromatic or tertiary alkyl amine oxidized to a corresponding N-oxide, wherein the aromatic amine is Ar oxidized to a corresponding N-oxide where Ar is a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; wherein the heterocyclic ring contains 1–6 heteroatom(s) selected from the group consisting of O, N, S, and a combination thereof wherein at least one of the heteroatoms is N, and wherein the alkyl amine is oxidized to a corresponding N-oxide where alkyl is a $C_1$–$C_6$ straight or branched chain alkyl or alkenyl which is optionally substituted in one or more positions with $C_1$–$C_6$ straight or branched chain alkyl or alkenyl, or $C_3$–$C_8$ cycloalkyl, or $C_5$–$C_7$ cycloalkenyl, or hydroxyl, or carbonyl oxygen, or with Ar, where said alkyl, alkenyl, cycloalkyl, cycloalkenyl, or Ar group is optionally substituted with $C_1$–$C_4$ alkyl, $C_1$–$C_4$ alkenyl, or hydroxy, or carbonyl oxygen, or wherein any of the carbon atoms of said alkyl, alkenyl, cycloalkyl, cycloalkenyl, or Ar group is optionally replaced with O, NH, $NR_1$, S, SO, or $SO_2$;

Ar is selected from the group consisting of pyrrolidinyl, pyridyl, pyrimidyl, pyrazyl, pyridazyl, quinolinyl, and isoquinolinyl; and, $R_1$ is hydrogen, ($C_1$–$C_4$)-straight or branched chain alkyl, ($C_3$–$C_4$)-straight or branched chain alkenyl or alkynyl, or $R_1$ is Y—Z as defined above.

6. A pharmaceutical composition comprising a neurotrophically effective amount of the compound of claim 5 and a pharmaceutically acceptable carrier.

7. A method of stimulating the growth of damaged neurons in an animal, comprising:
   administering to the animal a neurotrophically effective amount of the compound of claim 5.

8. A method of promoting neuronal regeneration in an animal, comprising:
   administering to the animal a neurotrophically effective amount of the compound of claim 5.

9. A compound of formula III comprising:

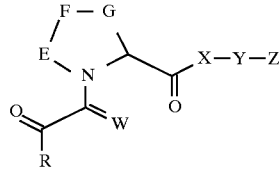

or a pharmaceutically acceptable salt thereof, wherein:
   E, F, and G are independently $CH_2$;
   W is O, S, $CH_2$, or $H_2$;
   R is a $C_1$–$C_6$ straight or branched chain alkyl or alkenyl group optionally substituted with $C_3$–$C_8$ cycloalkyl, $C_3$ or $C_5$ cycloalkyl, $C_5$–$C_7$ cycloalkenyl, or $Ar_1$, where said alkyl, alkenyl, cycloalkyl, or cycloalkenyl groups may be optionally substituted with $C_1$–$C_4$ alkyl, $C_1$–$C_4$ alkenyl, or hydroxy, and where $Ar_1$ is selected from the group consisting of 1-napthyl, 2-napthyl, 1-indolyl, 2-indolyl, 2-furyl, 3-furyl, 2-thienyl, 3-thienyl, 2-pyridyl, 3-pyridyl, 4-pyridyl, or phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkenyloxy, phenoxy, benzyloxy, and amino;
   X is O, NH, $NR_1$, S, $CH_2$, $CHR_1$, or $C(R_1)_2$;
   Y is a direct bond, or a $C_1$–$C_6$ straight or branched chain alkyl or alkenyl which is optionally substituted in one or more positions with $C_1$–$C_6$ straight or branched chain alkyl or alkenyl, or $C_3$–$C_8$ cycloalkyl, or $C_5$–$C_7$ cycloalkenyl, or hydroxyl, or carbonyl oxygen, or with Ar, where said alkyl, alkenyl, cycloalkyl, cycloalkenyl, or Ar group is optionally substituted with $C_1$–$C_4$ alkyl, $C_1$–$C_4$ alkenyl, or hydroxy, or carbonyl oxygen, or wherein any of the carbon atoms of said alkyl, alkenyl, cycloalkyl, cycloalkenyl, or Ar group is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group; and Z is an aromatic or tertiary alkyl amine oxidized to a corresponding N-oxide, wherein the aromatic amine is Ar oxidized to a corresponding N-oxide where Ar is a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; wherein the heterocyclic ring contains 1–6 heteroatom(s) selected from the group consisting of O, N, S, and a combination thereof wherein at least one of the heteroatoms is N, and wherein the alkyl amine is oxidized to a corresponding N-oxide where alkyl is a $C_1$–$C_6$ straight or branched chain alkyl or alkenyl which is optionally substituted in one or more positions with $C_1$–$C_6$ straight or branched chain alkyl or alkenyl, or $C_3$–$C_8$ cycloalkyl, or $C_5$–$C_7$ cycloalkenyl, or hydroxyl, or carbonyl oxygen, or with Ar, where said alkyl, alkenyl, cycloalkyl, cycloalkenyl, or Ar group is optionally substituted with $C_1$–$C_4$ alkyl, $C_1$–$C_4$ alkenyl, or hydroxy, or carbonyl oxygen, or wherein any of the carbon atoms of said alkyl, alkenyl, cycloalkyl, cycloalkenyl, or Ar group is optionally replaced with O, NH, $NR_1$, S, SO, or $SO_2$;

Ar is selected from the group consisting of pyrrolidinyl, pyridyl, pyrimidyl, pyrazyl, pyridazyl, quinolinyl, and isoquinolinyl; and, $R_1$ is hydrogen, ($C_1$–$C_4$)-straight or branched chain alkyl, ($C_3$–$C_4$)-straight or branched chain alkenyl or alkynyl, or $R_1$ is Y—Z as defined above.

10. A pharmaceutical composition comprising a neurotrophically effective amount of the compound of claim 9 and a pharmaceutically acceptable carrier.

11. A method of stimulating the growth of damaged neurons in an animal, comprising:
   administering to the animal a neurotrophically effective amount of the compound of claim 9.

12. A method of promoting neuronal regeneration in an animal, comprising:
   administering to the animal a neurotrophically effective amount of the compound of claim 9.

13. A compound of formula IV comprising:

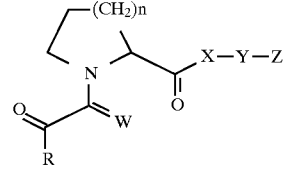

or a pharmaceutically acceptable salt thereof, wherein:
   n is 1, 2 or 3 forming a 5–7 member heterocyclic ring;
   W is O, S, $CH_2$, or $H_2$;
   R is a $C_1$–$C_6$ straight or branched chain alkyl or alkenyl group optionally substituted with $C_3$–$C_8$ cycloalkyl, $C_3$ or $C_5$ cycloalkyl, $C_5$–$C_7$ cycloalkenyl, or $Ar_1$, where said alkyl, alkenyl, cycloalkyl, or cycloalkenyl groups may be optionally substituted with $C_1$–$C_4$ alkyl, $C_1$–$C_4$ alkenyl, or hydroxy, and where $Ar_1$ is selected from the group consisting of 1-napthyl, 2-napthyl, 1-indolyl, 2-indolyl, 2-furyl, 3-furyl, 2-thienyl, 3-thienyl, 2-pyridyl, 3-pyridyl, 4-pyridyl, or phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkenyloxy, phenoxy, benzyloxy, and amino;

X is O, NH, $NR_1$, S, $CH_2$, $CHR_1$, or $C(R_1)_2$;

Y is a direct bond, or a C1–$C_6$ straight or branched chain alkyl or alkenyl which is optionally substituted in one or more positions with $C_1$–$C_6$ straight or branched chain alkyl or alkenyl, or $C_3$–$C_8$ cycloalkyl, or $C_5$–$C_7$ cycloalkenyl, or hydroxyl, or carbonyl oxygen, or with Ar, where said alkyl, alkenyl, cycloalkyl, cycloalkenyl, or Ar group is optionally substituted with $C_1$–$C_4$ alkyl, $C_1$–$C_4$ alkenyl, or hydroxy, or carbonyl oxygen, or wherein any of the carbon atoms of said alkyl, alkenyl, cycloalkyl, cycloalkenyl, or Ar group is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group; and Z is an aromatic or tertiary alkyl amine oxidized to a corresponding N-oxide, wherein the aromatic amine is Ar oxidized to a corresponding N-oxide where Ar is a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; wherein the heterocyclic ring contains 1–6 heteroatom(s) selected from the group consisting of O, N, S, and a combination thereof wherein at least one of the heteroatoms is N, and wherein the alkyl amine is oxidized to a corresponding N-oxide where alkyl is a $C_1$–$C_6$ straight or branched chain alkyl or alkenyl which is optionally substituted in one or more positions with $C_1$–$C_6$ straight or branched chain alkyl or alkenyl, or $C_3$–$C_8$ cycloalkyl, or $C_5$–$C_7$ cycloalkenyl, or hydroxyl, or carbonyl oxygen, or with Ar, where said alkyl, alkenyl, cycloalkyl, cycloalkenyl, or Ar group is optionally substituted with $C_1$–$C_4$ alkyl, $C_1$–$C_4$ alkenyl, or hydroxy, or carbonyl oxygen, or wherein any of the carbon atoms of said alkyl, alkenyl, cycloalkyl, cycloalkenyl, or Ar group is optionally replaced with O, NH, $NR_1$, S, SO, or $SO_2$;

Ar is selected from the group consisting of pyrrolidinyl, pyridyl, pyrimidyl, pyrazyl, pyridazyl, quinolinyl, and isoquinolinyl; and, $R_1$ is hydrogen, ($C_1$–$C_4$)-straight or branched chain alkyl, ($C_3$–$C_4$)-straight or branched chain alkenyl or alkynyl, or $R_1$ is Y—Z as defined above.

14. A pharmaceutical composition comprising a neurotrophically effective amount of the compound of claim 13 and a pharmaceutically acceptable carrier.

15. A method of stimulating the growth of damaged neurons in an animal, comprising:

administering to the animal a neurotrophically effective amount of the compound of claim 13.

16. A method of promoting neuronal regeneration in an animal, comprising:

administering to the animal a neurotrophically effective amount of the compound of claim 13.

17. A compound selected from the group consisting of:

3-(2-Pyridyl)-1-propyl(2S)-1-(1,1-Dimethyl-1,2-dioxopentyl)-2-pyrrolidinecarboxylate, N-oxide;

3-(3-Pyridyl)-1-propyl(2S)-1-(1,1-Dimethyl-1,2-dioxopentyl)-2-pyrrolidinecarboxylate, N-oxide;

3-(4-Pyridyl)-1-propyl(2S)-1-(1,1-Dimethyl-1,2-dioxopentyl)-2-pyrrolidinecarboxylate, N-oxide;

3-(2-Quinolyl)-1-propyl(2S)-1-(1,1-Dimethyl-1,2-dioxopentyl)-2-pyrrolidinecarboxylate, N-oxide;

3-(3-Quinolyl)-1-propyl(2S)-1-(1,1-Dimethyl-1,2-dioxopentyl)-2-pyrrolidinecarboxylate, N-oxide; and 3-(4-Quinolyl)-1-propyl(2S)-1-(1,1-Dimethyl-1,2-dioxopentyl)-2-pyrrolidinecarboxylate, N-oxide.

18. A pharmaceutical composition comprising a neurotrophically effective amount of the compound of claim 17 and a pharmaceutically acceptable carrier.

19. A method of stimulating the growth of damaged neurons in an animal, comprising:

administering to the animal a neurotrophically effective amount of the compound of claim 17.

20. A method of promoting neuronal regeneration in an animal, comprising:

administering to the animal a neurotrophically effective amount of the compound of claim 17.

* * * * *

UNITED STATES PATENT AND TRADEMARK OFFICE
CERTIFICATE OF CORRECTION

PATENT NO. : 5,846,979
DATED : December 8, 1998
INVENTOR(S) : Hamilton, Steiner and Burak It is certified that error appears in the above-identified patent and that said Letters Patent is hereby corrected as shown below:

Title page,
Item [56], References Cited, U.S. PATENT DOCUMENTS, for Patent No. 5,330,993, after "Armistead" please insert -- et al. --.
OTHER PUBLICATIONS, please insert,
-- Stocks, M. et al., "The contribution to the binding of the pyranoside substituents in the excised binding domain of FK-506," *Bioorg. Med. Chem. Lett.*, 1994, vol. 4, no. 12, pp. 1457-1460. --.

Column 3,
Line 31, after "Y is a direct bond, or a" and before "straight or branched chain", please replace "$C_1$-$C_6$" with -- C1-$C_6$ --.

Column 4,
Line 40, after "Y is a direct bond, or a" and before "straight or branched chain", please replace "$C_1$-$C_6$" with -- C1-$C_6$ --.

Column 8,
Line 51, after "as $C_1$-$C_3$, $C_1$-$C_4$, $C_1$-$C_5$, $C_1$-$C_6$, $C_2$-$C_4$, $C_2$-$C_5$", please replace "$C_2$-C6," with -- $C_2$-$C_6$, --.

Column 9,
Line 52, after "effect or result and includes without" and before "stimulating", please replace "limitaion" with -- limitation --.

Column 12,
Line 34, after "Topical application for the lower intestinal tract" and before "be", please replace "an" with -- can --.

Column 13,
Line 52, after "vitro assays. In studies to directly" and before "the rate of", please replace "asses" with -- assess --.

UNITED STATES PATENT AND TRADEMARK OFFICE
CERTIFICATE OF CORRECTION

PATENT NO.   : 5,846979
DATED        : December 8, 1998
INVENTOR(S)  : Hamilton, Steiner and Burak It is certified that error appears in the above-identified patent and that said Letters Patent is hereby corrected as shown below:

Column 14,
Line 56, after "striatum of animals receiving" and before "the", please remove "of animals receiving".

Signed and Sealed this

Nineteenth Day of November, 2002

*Attest:*

*Attesting Officer*

JAMES E. ROGAN
*Director of the United States Patent and Trademark Office*